(12) United States Patent
Brennan et al.

(10) Patent No.: US 12,303,612 B2
(45) Date of Patent: May 20, 2025

(54) SOFT TISSUE IMPLANT POCKET (71) Applicant: POLYNOVO BIOMATERIALS PTY LIMITED, Victoria (AU)

(72) Inventors: Paul Brennan, Victoria (AU); Timothy Graeme Moore, Victoria (AU)

(73) Assignee: POLYNOVO BIOMATERIALS PTY LIMITED, Victoria (AU)

( * ) Notice: Subject to any disclaimer, the term of this patent is extended or adjusted under 35 U.S.C. 154(b) by 0 days.

(21) Appl. No.: 16/955,942

(22) PCT Filed: Dec. 21, 2018

(86) PCT No.: PCT/AU2018/051385
§ 371 (c)(1),
(2) Date: Jun. 19, 2020

(87) PCT Pub. No.: WO2019/119060
PCT Pub. Date: Jun. 27, 2019

(65) Prior Publication Data
US 2021/0069374 A1    Mar. 11, 2021

(30) Foreign Application Priority Data
Dec. 22, 2017  (AU) .................. 2017905178

(51) Int. Cl.
A61F 2/12    (2006.01)
A61L 27/18   (2006.01)
(Continued)

(52) U.S. Cl.
CPC .............. *A61L 27/18* (2013.01); *A61F 2/12* (2013.01); *A61L 27/56* (2013.01); *A61L 27/58* (2013.01);
(Continued)

(58) Field of Classification Search
CPC ............... A61F 2/12; A61F 2210/0004; A61F 2210/0076; A61F 2002/0086;
(Continued)

(56) References Cited

U.S. PATENT DOCUMENTS 6,913,626 B2 * 7/2005 McGhan ............... A61F 2/12
                                                623/23.72
2004/0093081 A1 * 5/2004 Nilsson ............... A61F 2/30756
                                                623/13.18
(Continued)

FOREIGN PATENT DOCUMENTS

EP    1537883 B1    4/2008
WO   2009026387 A1  2/2009
(Continued)

OTHER PUBLICATIONS

Urgun-Demirtas et al., Laboratory investigation of biodegradability of a polyurethane foam under anaerobic conditions, (Aug. 2007) Polymer Degradation and Stability, V.92, pp. 1599-1610 (Year: 2007).*

(Continued)

*Primary Examiner* — Brian E Pellegrino
(74) *Attorney, Agent, or Firm* — POLSINELLI PC (57) ABSTRACT There is provided a soft tissue implant pocket which reduces the incidence of capsular contracture. The pocket is manufactured from a biodegradable, biocompatible polyurethane foam. The polyurethane contains biodegradable polyols and the foam has a pore size configured for cellular infiltration. The soft tissue implant pocket find use in, for example, breast augmentation and reconstruction.

16 Claims, 2 Drawing Sheets (51) Int. Cl.
- *A61L 27/56* (2006.01)
- *A61L 27/58* (2006.01)
- *C08G 18/42* (2006.01)
- *C08G 18/48* (2006.01)

(52) U.S. Cl.
CPC ..... *C08G 18/4266* (2013.01); *C08G 18/4829* (2013.01); *A61F 2210/0004* (2013.01); *A61F 2210/0071* (2013.01); *A61F 2210/0076* (2013.01); *A61F 2230/0071* (2013.01); *A61F 2250/003* (2013.01); *A61F 2250/0051* (2013.01)

(58) Field of Classification Search
CPC ... A61F 2002/30757; A61F 2220/0008; A61L 27/56; A61L 27/58; A61B 17/562
USPC ............................................. 623/8
See application file for complete search history.

(56) References Cited

U.S. PATENT DOCUMENTS

| | | |
|---|---|---|
| 2004/0148024 A1 | 7/2004 | Williams |
| 2009/0099600 A1 | 4/2009 | Moore et al. |
| 2010/0249924 A1 | 9/2010 | Powell et al. |
| 2010/0256777 A1 | 10/2010 | Datta et al. |
| 2011/0264213 A1* | 10/2011 | DeMiranda ............... A61F 2/12 623/8 |
| 2011/0309541 A1 | 12/2011 | Thompson et al. |
| 2012/0010726 A1* | 1/2012 | Bluecher ............... A61F 2/0063 623/23.72 |
| 2013/0096676 A1 | 4/2013 | Boegershausen et al. |
| 2014/0039617 A1* | 2/2014 | Maxwell .................. A61F 2/12 623/8 |
| 2014/0242258 A1 | 8/2014 | Goraltchouk et al. |
| 2015/0112434 A1* | 4/2015 | Felix ....................... A61L 27/58 623/8 |

FOREIGN PATENT DOCUMENTS

| | | |
|---|---|---|
| WO | 2010111458 A2 | 9/2010 |
| WO | 2015006737 A1 | 1/2015 |
| WO | 2017037649 A1 | 3/2017 |

OTHER PUBLICATIONS

Canadian Office Action issued on Aug. 4, 2021 for corresponding Canadian Application No. 3086253.

European Search Report issued on Aug. 16, 2021 for corresponding European Application No. 18890448.6.

International Search Report and Written Opinion issued on Apr. 3, 2019 for corresponding PCT Application No. PCT/AU2018/051385.

Stefano Pompei et al., "The Modern Polyurethane-Coated Implant in Brest Augmentation: Long-Term Clinical Experience," Aesthetic Surgery Journal, vol. 36, No. 10, 2016, pp. 1124-1129.

Japanese Office Action issued on Jan. 31, 2023 for corresponding Japanese Application No. 2020-554331.

* cited by examiner

SOFT TISSUE IMPLANT POCKET

FIELD

This disclosure relates to a soft tissue implant pocket which reduces the incidence of capsular contracture and also reduces movement of the implant. The pocket comprises a biodegradable, biocompatible polyurethane foam and finds use in, for example, breast augmentation and reconstruction.

BACKGROUND

Soft tissue implants are extensively used for cosmetic, aesthetic, and reconstructive purposes. One potential adverse event arising from the introduction of a soft tissue implant, in some cases, is capsular contracture. Shortly after an implant is introduced, the body's natural inflammatory response begins to deposit collagen around the implant in the form of a fibrous capsule.

Problems with capsular formation and contracture occur in relation to many implant types, such as pacemakers, dura matter substitutes, implantable cardiac defibrillators as well as breast and other aesthetic implants.

Capsular contracture in breast augmentation develops when internal scar tissue forms a tight or constricting capsule around a breast implant, contracting it until it becomes misshapen and hard. As a result, the breast may feel painful and hard and the capsule may affect the appearance or shape of the breast. This can occur in respect of both silicone and saline implants.

Capsular contracture of breast implants is the most common indicator of further surgery. Reported rates of clinically significant capsular contracture are between 15 to 45% (Incidence of capsular contracture in silicone versus saline cosmetic augmentation mammoplasty: A meta-analysis, Y. El-Sheik et al, Can J Plast Surg Vol 16, No 4, 211).

Implants with smooth surfaces suffer most from capsular formation and contracture and surface texturing has been used in an effort to reduce contracture. In some circumstances, and particularly where the surface morphology of the implant is not texturally consistent, collagen formation can be uneven leading to physically uncomfortable and visually unsightly formation of lumps, 'seams' or an uneven external body surface.

In this regard polyurethane textured coatings have been used in an effort to reduce capsular formation and contracture (Polyurethane-coated Breast Implants Revisited: A 30-Year Follow-Up, N. Castel et al, Arch Plast Surg 2015, 42, 186.)

However in 1992 the Food and Drug Administration (FDA) announced a moratorium on the use of silicone breast implants citing their possible link to breast cancer. Also, polyurethanes derived from aromatic isocyanates have been shown to degrade to potentially carcinogenic by-products in vitro.

As such, there is a need in the field for means for reducing or even eliminating capsular formation and contracture using products that are biocompatible. The present disclosure addresses these needs.

The reference in this specification to any prior publication (or information derived from it), or to any matter which is known, is not, and should not be taken as an acknowledgement or admission or any form of suggestion that the prior publication (or information derived from it) or known matter forms part of the common general knowledge in the field of endeavour to which this specification relates.

SUMMARY

In a first aspect the present disclosure provides a soft tissue implant pocket comprising an inner surface, an outer surface and an opening sized to receive an implant; wherein at least the outer surface of the pocket comprises a polyurethane foam, said foam comprising a pore structure configured for cellular infiltration.

In a second aspect the present disclosure provides a soft tissue implant comprising: a soft tissue implant pocket comprising an inner surface and an outer surface; and an implant sealed within the pocket; wherein at least the outer surface of the pocket comprises a polyurethane foam, said foam comprising a pore structure configured for cellular infiltration.

In some embodiments the inner surface of the implant pocket comprises a polyurethane foam. In other words the structural material of the pocket may consist essentially of a polyurethane foam.

In other embodiments the foam defining the inner surface and the foam defining the outer surface of the implant pocket have a polyurethane liner located therebetween. In other words the pocket is constructed from, for example, two sheets of foam-liner-foam material. The liner provides strength to the pocket.

In some embodiments the polyurethane foam is fixed to the surface of the implant. In some embodiments the polyurethane foam is not fixed to the surface of the implant but is in intimate contact with the surface of the implant so as to minimize the space between the inner surface of the foam pocket and the surface of the implant.

The polyurethane foam may be biodegradable.

In some embodiments the pocket further comprises an inner polyurethane liner which lines the inner surface of the pocket.

In another aspect the present disclosure provides a soft tissue impact pocket wherein the pocket is constructed from:
  (a) two or more biodegradable polyurethane foam layers; and
  (b) one or more polyurethane liners;
wherein the polyurethane liner is positioned between the foam layers; and
wherein said foam layers comprise a pore structure configured for cellular infiltration.

The soft tissue implant pocket is advantageous as, in use, it minimizes capsular contracture.

The soft tissue implant pocket possesses a number of further advantages including one or more of the following:
  the pocket is conformable to different implant shapes
  the pocket minimizes movement and/or rotation and/or dislocation of the implant
  the outside surface of the pocket is substantially free of kinks and overlaps
  the polyurethane foam is substantially resistant to shrinkage in vivo
  the polyurethane foam enables tissue integration
  the polyurethane foam may degrade over time so that it need not be surgically removed
  the polyurethane foam is biocompatible.

The implant pocket may be formed from one contiguous sheet of foam which may be moulded, formed or folded to form a pocket. Alternatively, it may be formed from more than one sheet of foam. When more than one sheet of foam is used the sheets may be fused together proximate the edges of the foam so as to form a pocket having seams. In one embodiment the bonded edges of the pocket are external of the pocket. In another embodiment, the bonded edges of the pocket are internal of the pocket. The location of the seams may assist in reducing capsular contraction.

In other embodiments the seams are neither external or internal and do not substantially protrude.

The polyurethane foam may comprise a thermoset polyurethane or may comprise a thermoplastic polyurethane. Preferably the polyurethane foam comprises a thermoset polyurethane. Preferably the foam comprises a cross-linked polyurethane.

The polyurethane liner may comprise a thermoset polyurethane or may comprise a thermoplastic polyurethane. Preferably the polyurethane liner comprises a thermoplastic polyurethane.

The polyurethane liner may comprise a biodegradable polyurethane or a non-degradable polyurethane. The polyurethane liner may be designed to degrade at a different rate to the polyurethane foam or at substantially the same rate.

As used herein, the term 'biodegradable' refers generally to the capability of being broken down in the normal functioning of living organisms/tissue, preferably into innocuous, non-toxic or biocompatible products.

In some embodiments the polyurethane foam may degrade faster than the polyurethane liner.

In some embodiments the liner provides a barrier to cellular infiltration such that cell growth, while occurring in the polyurethane foam, cannot interact with the surface of the implant.

The soft tissue implant pocket finds use as a covering for a variety of implants. The pocket may be used as a covering for silicone or saline breast implants.

The polyurethane foam may shrink less than 20%, or less than 15%, or less than 10%, or less than 5%, independently, in any single surface area after 10 days under in vivo conditions.

The polyurethane foam may shrink less than 20%, or less than 15%, or less than 10%, or less than 5%, independently, in any single surface area, after 20 days under in vivo conditions or after 60 days under in vivo conditions, or after 90 days under in vivo conditions, or after 120 days under in vivo conditions, or after 200 days under in vivo conditions, or after 1 year under in vivo conditions, or after 2 years under in vivo conditions.

The polyurethane liner may shrink less than 20%, or less than 15%, or less than 10%, or less than 5%, in any single surface area after 10 days under in vivo conditions.

The polyurethane liner may shrink less than 20%, or less than 15%, or less than 10%, or less than 5%, independently, in any single surface area, after 20 days under in vivo conditions or after 60 days under in vivo conditions, or after 90 days under in vivo conditions, or after 120 days under in vivo conditions, or after 200 days under in vivo conditions, or after 1 year under in vivo conditions, or after 2 years under in vivo conditions.

The polyurethane foam of the soft tissue implant pocket may have a thickness between about 0.1 mm and about 10 mm, or between about 0.2 mm and about 5 mm, or between about 0.3 mm and about 3 mm, or between about 0.3 mm and about 2 mm. The foam may have a thickness of less than about 10 mm, or less than about 6 mm, or less than about 4 mm, or less than about 2 mm, or less than about 1 mm, or less than about 0.5 mm.

Preferably, the foam has a thickness of between 0.3 mm and about 3 mm.

The polyurethane liner may have a thickness between about 20 μm and about 1000 μm, or between about 50 μm and about 500 μm, or between about 50 μm and about 400 μm.

In some embodiments the foam may have a thickness between about 0.3 mm and about 3 mm and the liner may have a thickness between about 50 μm and about 400 μm.

In some embodiments the foam may have a thickness between about 0.3 mm and about 1 mm and the liner may have a thickness between about 100 μm and about 300 μm.

In some embodiments the foam may be a non-reticulated foam. In some embodiments the foam may be a reticulated foam. The foam may have interconnecting pores. Preferably the foam is a non-reticulated foam.

As used herein the term 'non-reticulated' polyurethane foam refers to a polyurethane foam which has not been subjected to a post manufacturing step to remove cell windows using either chemicals (such as alkaline solution), heat (such as controlled combustion of hydrogen and oxygen), or solvents.

In some embodiments the foam may have a density between 3 g/100 ml and 12 g/100 ml, or between 4 g/100 ml and 10 g/100 ml, or between 5 g/100 ml and 8 g/100 ml.

In some embodiments the porosity of the foam may be greater than 50%, or greater than 75%, or from 80 to 95%, or from 95 to 99.9%. It is desirable that the porosity should be as high as possible while maintaining other mechanical specifications. If the porosity is too low the pores may not interconnect. If the porosity is too high the structural integrity of the foam may be mechanically compromised.

In some embodiments the average pore size of the foams may be greater than 50 μm, or greater than 75 or greater than 100 μm, or greater than 200 μm, or in the range 100 to 600 μm, or in the range 100 to 400 μm.

In some embodiments the average pore size of the foam is in the range 50 to 600 μm, or in the range 60 to 600 μm, or in the range 70 to 600 μm, or in the range 75 to 400 μm, or in the range 75 to 300 μm, or in the range 100 to 300 μm.

Preferably the average pore size of the foam is greater than 75 μm, more preferably between about 100 and about 300 μm.

More preferably the average pore size is in the range from about 100 to about 300 μm.

In some embodiments the soft tissue implant pocket may comprise one or more further layers disposed between the foam and the liner. The one or more further layers may be an adhesive layer and/or a further foam layer.

In some embodiments the soft tissue implant pocket is substantially free of aromatic functionality. In this context, 'substantially free' means that the soft tissue implant pocket contains less than 0.1 wt. % of aromatic functionality based on the total weight of the pocket, or less than 0.01 wt. %, or less than 0.001 wt. %, or zero %.

The soft tissue implant pocket may be of any shape. Preferred shapes include spherical, spheroidal, ovoidal and the like.

Polyurethane Foam

The biodegradable polyurethane foam may be biodegradable within a living organism to biocompatible degradation products.

The polyurethane foam may be in vivo degradable. The polyurethane foam may be degradable at temperatures between about 35° C. and about 42° C.

The polyurethane foam may degrade by hydrolysis. The polyurethane foam may degrade by hydrolysis of ester functionalities.

Foam Polyols

The polyurethane foam may be derived from one or more biodegradable polyols and one or more isocyanates. Alternatively, the polyurethane foam may be derived from a mixture of one or more biodegradable polyols and one or more non-biodegradable polyols and one or more isocyanates. Preferably the biodegradable polyols are polyester polyols.

The foam may be derived from one or more biodegradable polyols having a molecular weight of less than or equal to about 2000 Daltons, or less than or equal to about 1500 Daltons, or less than or equal to about 1300 Daltons.

The biodegradable polyols may have a molecular weight between about 200 and about 2,000 Daltons, or between about 200 and about 1,500 Daltons, or between about 200 and about 1,300 Daltons, or between about 600 and about 1500 Daltons, or between about 900 and about 1300 Daltons.

The biodegradable polyols may have a molecular weight of less than or equal to about 10,000 Daltons, or less than or equal to about 8,000 Daltons, or less than or equal to about 6,000 Daltons, or less than or equal to about 4,000 Daltons, or less than or equal to about 2,000 Daltons, or less than or equal to about 1,500 Daltons, or less than or equal to about 1,000 Daltons, or less than or equal to about 800 Daltons, or less than or equal to about 600 Daltons, or less than or equal to about 500 Daltons, or less than or equal to about 400 Daltons, or less than or equal to about 350 Daltons, or less than or equal to about 300 Daltons.

The biodegradable polyols may have a molecular weight of less than 500 Daltons or less than 400 Daltons or less than 350 Daltons, or less than 300 Daltons.

The biodegradable polyols may be in the liquid state at 20° C. and atmospheric pressure. Alternatively, the biodegradable polyols may be in the solid state at 20° C. and atmospheric pressure. In some embodiments the polyols may in the form of a mixture of solid and liquid at 20° C.

The biodegradable polyols may be derived from one or more polyol initiators and one or more hydroxy acids, diacids or cyclic esters and combinations thereof.

In some embodiments the biodegradable polyol may be derived from one or more polyol initiators and at least one hydroxy acid.

In some embodiments the biodegradable polyol may be derived from one or more polyol initiators and at least one diacid.

In some embodiments the biodegradable polyol may be derived from one or more polyol initiators and at least one cyclic ester.

In some embodiments the biodegradable polyol may be derived from one or more polyol initiators, at least one hydroxy acid and at least one diacid.

In some embodiments the biodegradable polyol may be derived from one or more polyol initiators, at least one hydroxy acid and at least one cyclic ester.

In some embodiments the biodegradable polyol may be derived from one or more polyol initiators, at least one diacid and at least one cyclic ester.

In some embodiments the biodegradable polyol may be derived from one or more polyol initiators, at least one hydroxyl acid, at least one diacid and at least one cyclic ester.

The one or more polyol initiators may be pentaerythritol, trimethylol propane, glycerol, 1,4-butanediol, ethylene glycol, sorbitol, glucose, sucrose, 1,2-propanediol, 1,3-propanediol, pentane diol, myoinositol, hexamethylenediol, heptanediol, octanediol, nonanediol, decanediol, dodecanediol, 2-ethyl-1,3-hexanediol (EHD), 2,2,4-trimethyl pentane-1,3-diol (TMPD), 1,4-cyclohexane dimethanol, diethylene glycol, dipropylene glycol, and combinations thereof.

Non-limiting examples of hydroxy acids include l-lactic acid, d-lactic acid, d,l-lactic acid, mandelic acid, phenyllactic acid, hydroxybutyric acid, hydroxyvaleric acid or glycolic acid and combinations thereof.

Non-limiting examples of cyclic esters include ε-caprolactone, glycolide, lactide, mandelide, and ρ-dioxanone and combinations thereof. The biodegradable polyols may be prepared via a ring-opening polymerisation reaction or a condensation reaction.

Non-limiting examples of diacids include oxalic acid, malonic acid, succinic acid, glutaric acid, adipic acid, pimelic acid, suberic acid, azelaic acid, sebacic acid, undecanedioic acid, dodecanedioic acid, tridecanedioic acid, and hexadecanedioic acid and combinations thereof.

The biodegradable polyols may be prepared via a ring-opening polymerisation reaction or a condensation reaction or via both a ring-opening polymerisation reaction and a condensation reaction.

The one or more non-biodegradable polyols may be a polyether polyol. The polyether polyol may be one or more of glycerol ethoxylate, glycerol propoxylate, glycerol ethoxylate-co-propoxylate, glycerol ethoxylate-block-propoxylate, pentaerythritol ethoxylate, pentaerythritol propoxylate and trimethylolpropane propoxylate.

The one or more non-biodegradable polyols may have a molecular weight of less than or equal to about 2000 Daltons, or less than or equal to about 1500 Daltons, or less than or equal to about 1300 Daltons.

The non-biodegradable polyols may have a molecular weight between about 200 and about 2,000 Daltons, or between about 200 and about 1,500 Daltons, or between about 200 and about 1,300 Daltons, or between about 600 and about 1500 Daltons, or between about 900 and about 1300 Daltons.

The non-biodegradable polyols may have a molecular weight of less than or equal to about 10,000 Daltons, or less than or equal to about 8,000 Daltons, or less than or equal to about 6,000 Daltons, or less than or equal to about 4,000 Daltons, or less than or equal to about 2,000 Daltons, or less than or equal to about 1,500 Daltons, or less than or equal to about 1,000 Daltons, or less than or equal to about 800 Daltons, or less than or equal to about 600 Daltons, or less than or equal to about 500 Daltons, or less than or equal to about 400 Daltons, or less than or equal to about 350 Daltons, or less than or equal to about 300 Daltons.

The non-biodegradable polyols may have a molecular weight of less than 500 Daltons or less than 400 Daltons or less than 350 Daltons, or less than 300 Daltons.

The biodegradable polyols impart biodegradability to the foam. The polyols may be prepared by condensation polymerization or ring-opening polymerization with a high proportion of initiator (or starter) to control the molecular weight. The amount of initiator may range from between 1 mole of initiator per 200 g of polyol and 1 mole of initiator per 5000 g of polyol, or between 1 mole of initiator per 500 g polyol and 1 mole of initiator per 2000 g of polyol. Non-limiting examples of suitable monomers for the initiator include pentaerythritol (4-arm), trimethylol propane (3-arm), glycerol (3-arm), 1,4-butanediol (2-arm), myo-inositol (6-arm). Mixtures of initiators may be utilized. Mixtures of polyols may be utilized. It may be preferable to minimize the number of components. However, in some instances it may be advantageous to utilise more than one polyol, or more than two. The polyol may have a hydroxyl functionality of 2 or more. Polyols having only a single hydroxyl functionality, when used in large amounts, may not result in an adequate foam. However, minor amounts may be used to adjust the properties of the foam, for example, adding a few percent of a mono-hydroxyl compound which has a long-chain lipophilic chain, may influence the hydrophobicity/hydrophilicity of the foam.

The rate of degradation of the foam may be controlled by altering the ratio of biodegradable polyol to that of non-biodegradable polyol. By reducing or eliminating a non-biodegradable polyol from the formulation, faster degrading foams may be produced which may be desirable in certain applications. Monomer selection may also influence the rate of degradation due to kinetic differences in the rate of hydrolysis of different ester linkages.

Biodegradable and non-biodegradable polyols have different functions in the foam of the soft tissue implant pocket. Non-biodegradable polyols may be selected from the polyether polyols, for example, glycerol ethoxylate, glycerol propoxylate and glycerol ethoxylate-co-propoxylate. Such non-biodegradable polyols may stabilize the foam through the introduction of non-biodegradable function. Further they may provide a mechanism to control the hydrophilic/hydrophobic balance through, for example, the ethoxylate/propoxylate content. They may also improve foam resilience by lowering the glass transition temperature (Tg).

Biodegradable polyols may be solid at lower molecular weights than non-biodegradable polyols, for example, polycaprolactone diol of 500 molecular weight is a solid at room temperature, whereas poly(propylene glycol) remains a liquid to a much higher molecular weight. High molecular weight non-biodegradable liquid polyols may act as a 'filler' to reduce the isocyanate content and hence reduce the likelihood of scorching through excessive exothermic reaction during preparation of the foams.

Biodegradable polyols may be derived from one or more polyol initiators and at least one hydroxy acid and/or cyclic ester. They may contribute to lowering the Tg in circumstances where the Tg has not been reduced sufficiently by the non-biodegradable polyether. The polyol may be a 3-arm, glycerol-initiated polyol based on ε-caprolactone and one of glycolic acid or lactic acid. The amount of the CL:(LA and/or GA) may influence both the glass transition as well as the degradation time. More caprolactone lowers the Tg and increases the degradation time. The molecular weight may be 800-1200 Daltons. The molecular weight may be low enough to be liquid, but high enough to not require high amounts of isocyanate for reaction so as to avoid scorching.

Foam Isocyanates

The polyurethanes from which the foam are prepared may be derived from one or more biodegradable polyols and one or more isocyanates. The molar ratio of isocyanate functions to hydroxy and other isocyanate reactive functions from which the foam is derived (the isocyanate index) may be less than or equal to 1.0, or less than or equal to 0.9, or less than or equal to 0.8, or less than or equal to 0.7, or less than or equal to 0.6. The isocyanate index may be between 0.4 and 1.0, or between 0.6 and 0.9.

The polyurethane foam may be derived from polyols and isocyanates having an isocyanate content (that is, the content of NCO functions) of less than 20% by weight, or less than 19%, or less than 18%, or less than 17%, or less than 16%, or less than 15%, or less than 14%, or less than 13%, or less than 12%, or less than 11%, or less than 10%, or less than 9%, or less than 8% by weight based on the total weight of polyols and isocyanates. The foam may have an isocyanate content of between 5% and 20%, or between 8% and 17%, or between 11% and 14% by weight based on the total weight of polyol and isocyanate.

The degradation products from aliphatic isocyanates (such as ethyl lysine diisocyanate (ELDI)) are generally considered to be more biocompatible than the degradation products from aromatic diisocyanates. Accordingly, isocyanates such as hexamethylene diisocyanate (HDI) and ELDI may be particularly suitable. Isophorone diisocyanate (IPDI) may also be used but may impart a higher glass transition temperature which may result in a stiffening of the foam. Combinations of isocyanates may be used and may in some instances be preferable, for example, glass transition can be adjusted by combinations of HDI and IPDI. Trimethylhexamethylenediisocyanate, 1,4-butane diisocyanate, methyl-lysine diisocyanate (MLDI) and other isocyanates commonly used in polyurethane synthesis may also be suitable.

Lowering the isocyanate index results in softer and weaker foams which degrade more quickly. Increasing the isocyanate index may increase the degradation time but results in stronger foams.

A biodegradable polyurethane foam is advantageous since it may be designed to include the properties of resilience, resistance to premature degradation, resistance to contraction, prevention of excessive acidic degradation products, biocompatibility, controlled water absorption, compatibility with other polyurethane layers and ease of incorporating additives during synthesis. The foams may be soft and conformable to a desired shape.

The foams may be designed to degrade at a specific rate. They may be designed to retain structural integrity for over, for example, three months or they may be designed to retain structural integrity for as little as, for example, a few days, even one or two days.

The polyurethane foam may degrade, under the conditions of ASTM F1635, such that the mass of the foam decreases by between about 10% and about 90% in a period of one year or less.

Alternatively, the mass of the foam may decrease by between about 10% and about 90% in a period of eleven months or less, or ten months or less, or nine months or less, or eight months or less, or seven months or less, or six months or less, or five months or less, or four months or less, or three months or less, or two months or less, or one month or less.

The rate of degradation, under the conditions of ASTM F1635, may be controlled through varying the nature and ratios of the components of the polyurethane foam. Accordingly, the polyurethane may be designed to degrade within a specific time period. This is advantageous in providing materials that are partially, fully, or substantially fully degradable in a specific time period, for example, when the functional aspects of the polyurethane foam layers are no longer required.

This is particularly useful where the polyurethane is targeted for in vivo applications as the polyurethane may not need to be surgically removed from a patient's body.

The rate of degradation of the foam may be controlled by altering the ratio of biodegradable polyol to non-biodegradable polyol or through choice of monomers. By reducing or eliminating a non-biodegradable polyol from the formulation, faster degrading materials may be produced which may be desirable in certain applications.

The foams may be derived from at least one prepolymer which may be prepared by contacting one or more biodegradable polyols and/or one or more polyol initiators with one or more polyisocyanates. Non-limiting examples of polyol initiators are, for example, pentaerythritol, trimethylol propane, glycerol, 1,4-butanediol and myo-inositol, ethylene glycol, sorbitol, glucose, sucrose, 1,2-propanediol and mixtures thereof. The foam may be derived from a mixture of such so-formed prepolymers and further polyisocyanate. The foam may contain less than 50% by weight of prepolymer and greater than 50% by weight of polyisocyanate based on the combined weight of these components. The foam may contain from less than 30% by weight of prepolymer and greater than 70% by weight of polyisocyanate based on the combined weight of these components. Foams prepared in this way advantageously may possess high strength and fine cell structure.

The foam may be derived from a biodegradable polyol having a molecular weight less than or equal to about 1300 Dalton and from polyols and polyisocyanates having an isocyanate (NCO) content of less than 20%, or less than 19%, or less than 18%, or less than 17%, or less than 16%, or less than 15%, or less than 14%, or less than 13%, or less than 12%, or less than 11%, or less than 10%, or less than 9%, or less than 8% by weight based on the total weight of polyols and polyisocyanates.

The foam may be derived from a biodegradable polyol and a non-biodegradable polyol wherein the molecular weight of the biodegradable polyol is less than our equal to about 1300 Dalton and from polyols and polyisocyanates having an isocyanate (NCO) content is less than 20%, or less than 19%, or less than 18%, or less than 17%, or less than 16%, or less than 15%, or less than 14%, or less than 13%, or less than 12%, or less than 11%, or less than 10%, or less than 9%, or less than 8% by weight based on the total weight of polyols and polyisocyanates.

The foam may be derived from a biodegradable polyol having a molecular weight less than or equal to about 1300 Dalton and from polyols and polyisocyanates having an isocyanate (NCO) content of less than 20%, or less than 19%, or less than 18%, or less than 17%, or less than 16%, or less than 15%, or less than 14%, or less than 13%, or less than 12%, or less than 11%, or less than 10%, or less than 9%, or less than 8% by weight based on the total weight of polyols and polyisocyanates and a molar ratio of isocyanate functions to hydroxy and other isocyanate reactive functions (the isocyanate index) less than or equal to 1.0.

The foam may be derived from a biodegradable polyol and a non-biodegradable polyol wherein the molecular weight of the biodegradable polyol is less than our equal to about 1300 Dalton and from polyols and polyisocyanates having an isocyanate (NCO) content is less than 20%, or less than 19%, or less than 18%, or less than 17%, or less than 16%, or less than 15%, or less than 14%, or less than 13%, or less than 12%, or less than 11%, or less than 10%, or less than 9%, or less than 8% by weight based on the total weight of polyols and polyisocyanates and a molar ratio of isocyanate functions to hydroxy and other isocyanate reactive functions (the isocyanate index) less than or equal to 1.0.

Various additives known in the fields of polyurethane foam technology and tissue engineering may be added to the foam. These additives may be added during or after synthesis of the foam. The additives in some cases may react during the foam synthesis and be incorporated covalently into the foam. Exemplary additives include antimicrobial agents, plasticizers, pore openers, antioxidants, antistatic agents, catalysts, fillers, flame retardants, softeners/flexibilisers, cell control agents, release agents, stabilizers, fillers, dyes, pigments, pigment dispersants, solvents, anaesthetics, cells, enzymes, proteins, growth factors, growth inhibitors, haemostatic agents and bioactive agents such as drugs. The additives may or may not be chemically bonded to the foam.

Catalysts

There are a large number of catalysts known in the field of polyurethane synthesis that may be used in the preparation of the polyurethanes of the present disclosure. Various catalysts may be used in the preparation of the compositions and these may provide different attributes. For example, dibutyltin dilaurate (DBTL), stannous octoate and amine-based catalysts, such as DABCO. Bismuth, zinc and titanium-based catalysts are also known to catalyze urethane formation effectively and exhibit low toxicity. COSCAT Z-22 is a zinc-based catalyst and is an example of a catalyst that can be used that has low toxicity and gives effective results. Mercury and lead-containing catalysts are effective but are considered toxic (non-biocompatible) and therefore unsuitable. Combinations of catalysts are known to be effective. Minimisation of catalyst amount is also desirable.

Surfactant

The function of the surfactant (stabilizer, foaming agent) is to assist in preventing the bubbles in the foam from bursting when they are formed during the reaction, which allows them to rise and create a stable foam which can then cure.

Surfactants may be siloxane-ether copolymers, fluoro-ether copolymers, or other amphiphilic compounds containing a hydrophobic portion and a hydrophilic portion. There are many commercial surfactants that have been specifically developed for polyurethane foams. Amounts used vary from 0.01% to 1.5% by mass of the overall formulation. Preferred amounts are in the range 0.01% to 0.20% of the formulation. The most suitable amount depends on the molecular weight of the surfactant and the composition and type, as well as the remainder of the formulation—some formulations may be more hydrophobic and some may be more hydrophilic and hence may require different amounts of stabilisation. Useful surfactants may be simple block copolymers and brush-type copolymers. It is straightforward for the skilled person to vary the concentration of surfactant and determine which concentration is most effective in stabilizing the foam layer.

Blowing Agent

The foams may be blown by any method known in the art. The blowing agent may be generated during formation of the foam and/or may be added as one or more further components. Water may be used in the formulation to react with isocyanate, thus forming a urea linkage and CO2 gas. The CO2 gas creates the bubbles and blows the foam. Temperature, mixing and choice of surfactant, for example, may all affect the size of the bubbles (cell size). Commercially, polyurethane foams range in pore size from microporous (low density shoe soles) through to open cell large-celled foams (for example in filters or foam mattresses). Desirable porosities may be obtained by using 0.1 to 4% by weight of water, preferably 1.0 to 1.5% by weight of water in the overall formulation. This results in an appropriate level of foaming. Less water results in a denser foam. Higher amounts of water may be useful, but there will be a limit where the mechanical properties are negatively affected and scorching becomes likely.

Pentane and other low-boiling hydrocarbons may also be suitable as blowing agents. Foams produced in this manner may be advantageously urea-free due to the absence of water. Desirably, the absence of water reduces the amount of isocyanate required to react in the formulation, which consequently reduces the amount of heat generated when the foam is produced. This is particularly advantageous in large scale preparations where the heat of reaction may be more difficult to dissipate from the foam.

The foam layers may independently comprise any one or more of the herein disclosed features in any combination.

Preparation of Polyurethane Foam

The foams may be simply prepared by a one-pot method. All the components may be combined and mixed with or without the application of heat, and the foam will rise and cure. Alternatively, the foams may be prepared by any of the continuous or semi-continuous processes well known in the art.

In one embodiment, one or more polyols or polyol initiators is/are first treated with a polyisocyanate to form a prepolymer. This prepolymer is in turn treated with further components so to form the foam. In another embodiment, further polyisocyanate over and above that utilized to form the prepolymer may be utilized.

In another embodiment, all components, apart from the polyisocyanate component(s) are mixed together to form one part. The polyisocyanate is then added so as to begin the reaction. This is advantageous in that the two parts are both stable prior to mixing them together.

The foam may be prepared in a solvent free process.

The foams may be advantageously prepared by a one-pot batch procedure which may require no isolation or purification of intermediate materials. The foams may be prepared from low cost raw materials.

Reticulation

In some instances it may be advantageous to reticulate the foam. Reticulation results in the removal of cell windows so as to increase the amount of open cell material. This may be advantageous when fluid transfer is a requirement. This may be performed in a special chamber (reticulation chamber) where hydrogen and oxygen are introduced to the foam and ignited to disrupt and remove any cell windows.

Cell openers or cell opening agents may be added to the foam mixture to, for example, disrupt the pore structure during the foaming process, thereby creating foams with a natural sponge structure. Cell openers may reduce the tightness and shrinkage of the foam, resulting in dimensionally stable foams with inter-connected pores. Cell openers and other reaction components of polyurethane foams are discussed, for example in Szycher, M, Szycher's Handbook of Polyurethanes, CRC Press, New York, N.Y., 9-6 to 9-8 (1999). Cell openers suitable for use include powdered divalent metal salts of long-chain fatty acids having from about 1-22 carbon atoms. Divalent metal salts of stearic acid, such as calcium and magnesium stearate, are examples of cell openers. The concentrations of cell openers in the resin mix may be in the range of approximately 0.1-7.0% by weight or in the range of approximately 0.3 to 1% by weight.

Bioactive Agents

Bioactive agents may optionally be added to the foam mix. As used herein, the term 'bioactive' refers generally to an agent, a molecule, or a compound that affects biological or chemical events in a host.

Polyurethane Liner

The polyurethane liner, when present, may consist of more than one layer. For example, the liner may be a laminate of two or more sheets of the same or different polyurethanes.

The liner may comprise a biodegradable polyurethane. The liner may be derived from one or more polyols, one or more isocyanates and one or more chain extenders. The chain extenders may be biodegradable or non-degradable.

In some embodiments the liner comprises an oriented polyurethane.

In some embodiments the liner comprises a biaxially oriented polyurethane.

In some embodiments the oriented polyurethane is annealed.

The liner should be flexible enough to conform to the shape of the foam of the soft tissue implant pocket. The liner may be composed of one or more layers of polyurethane.

The liner may be biodegradable or non-biodegradable but should preferably be biocompatible.

The liner may be a woven or non-woven layer of fibres as may be obtained for example by electrospinning.

Liners of 50-400 μm thickness offer a good balance between strength (increases with thickness), permeability (decreases with thickness) and handling (stiffer as it gets thicker). Additionally, the mass of the liner may become too high compared to the mass of the foam if it is too thick.

In some embodiments, the liner may be porous. The porosity may be imparted by introducing one or more apertures in the liner prior to construction of the laminate. Preferably the apertures are sized to allow cellular fluid to pass therethrough.

In some embodiments the size of the apertures may be between about 0.1 mm and about 5 mm, preferably between about 1 mm and about 5 mm.

Preferably the distance between individual apertures may be between about 0.5 mm and 5 mm, more preferably between about 1 mm and about 3 mm. Most preferably about 2 mm. The apertures are configured to permit tissue growth through the film and vascularization to occur throughout the implant pocket.

The soft tissue implant pocket may comprise a biocompatible and/or biodegradable adhesive located between the foam and the liner.

In other embodiments, no adhesive may be utilised and the liner may be fused directly onto the foam.

The polyurethane liner may be derived from:
one or more chain extenders represented by formula (1) or formula (2)

wherein $R_1$, $R_2$ and $R_3$ are independently selected from optionally substituted $C_{1-20}$ alkylene and optionally substituted $C_{2-20}$ alkenylene;
one or more aliphatic polyester polyols; and
one or more aliphatic diisocyanates.

The polyurethane liner may have a number average molecular weight ($M_w$) up to 200,000 Daltons, or up to 150,000 Daltons, or up to 100,000 Daltons, or up to 60,000 Daltons, or up to 40,000 Daltons, or up to 20,000 Daltons.

The polyurethane liner may have a number average molecular weight ($M_w$) between 2,000 and 200,000 Daltons, or between 5,000 and 150,000 Daltons or between 10,000 and 100,000 Daltons or between 20,000 and 100,000 Daltons or between 2,000 and 60,000 Daltons, or between 2,000 and 40,000 Daltons or between 2,000 and 20,000 Daltons.

The polyurethane may have a number average molecular weight ($M_n$) up to 100,000 Daltons, or up to 75,000 Daltons, or up to 50,000 Daltons, or up to 30,000 Daltons, or up to 20,000 Daltons, or up to 10,000 Daltons. Preferably, the number average molecular weight of the polyurethane is between 50,000 and 100,000 Daltons.

The polyurethane may have a polydispersity ($M_w/M_n$) between 1.0 and 4.0, or between 1.0 and 3.5, or between 1.5 and 3.0. Preferably the polydispersity is between 1.0 and 2.0.
Liner Polyols The polyols may have a molecular weight between about 200 and about 2,000 Daltons, or between about 200 and about 1,500 Daltons, or between about 200 and about 1,300 Daltons.

The polyols may have a molecular weight of less than or equal to about 10,000 Daltons, or less than or equal to about 8,000 Daltons, or less than or equal to about 6,000 Daltons, or less than or equal to about 4,000 Daltons, or less than or equal to about 2,000 Daltons, or less than or equal to about 1,500 Daltons, or less than or equal to about 1,000 Daltons, or less than or equal to about 800 Daltons, or less than or equal to about 600 Daltons, or less than or equal to about 500 Daltons, or less than or equal to about 400 Daltons, or less than or equal to about 350 Daltons, or less than or equal to about 300 Daltons.

The polyols may have a molecular weight of less than 500 Daltons or less than 400 Daltons or less than 350 Daltons, or less than 300 Daltons.

The polyols may be in the liquid state at 20° C. and atmospheric pressure. Alternatively, the polyols may be in the solid state at 20° C. and atmospheric pressure.

The polyols may be derived from one or more diol initiators and one or more hydroxy acids, diacids or cyclic esters and combinations thereof.

In one embodiment the polyol may be derived from one or more diol initiators and at least one hydroxy acid.

In one embodiment the polyol may be derived from one or more diol initiators and at least one diacid.

In one embodiment the polyol may be derived from one or more diol initiators and at least one cyclic ester.

In one embodiment the polyol may be derived from one or more diol initiators, at least one hydroxy acid and at least one diacid.

In one embodiment the polyol may be derived from one or more diol initiators, at least one hydroxy acid and at least one cyclic ester.

In one embodiment the polyol may be derived from one or more diol initiators, at least one diacid and at least one cyclic ester.

In one embodiment the polyol may be derived from one or more diol initiators, at least one hydroxyl acid, at least one diacid and at least one cyclic ester.

Non-limiting examples of the one or more diol initiators include ethylene glycol, 1,3-propanediol, 1,2-propanediol, 1,4-butanediol, pentanediol, hexamethylenediol, heptanediol, octanediol, nonanediol, decanediol, dodecanediol, 2-ethyl-1,3-hexanediol (EHD), 2,2,4-trimethyl pentane-1,3-diol (TMPD), 1,4-cyclohexane dimethanol, diethylene glycol, dipropylene glycol, and combinations thereof. Non-limiting examples of diacids include oxalic acid, malonic acid, succinic acid, glutaric acid, adipic acid, pimelic acid, suberic acid, azelaic acid, sebacic acid, undecanedioic acid, dodecanedioic acid, tridecanedioic acid, and hexadecanedioic acid and combinations thereof. Non-limiting examples of hydroxy acids include l-lactic acid, d-lactic acid, d,l-lactic acid, mandelic acid, phenyl-lactic acid, hydroxybutyric acid, hydroxyvaleric acid or glycolic acid and combinations thereof. Non-limiting examples of cyclic esters include ε-caprolactone, glycolide, lactide, mandelide, and ρ-dioxanone and combinations thereof. The polyols may be prepared via a ring-opening polymerisation reaction or a condensation reaction or via both a ring-opening polymerisation reaction and a condensation reaction.
Liner Chain Extenders In some embodiments R1, R2 and R3 of formulae (1) and (2) are independently selected from optionally substituted C1-6 alkylene and optionally substituted C2-6 alkenylene.

The term "optionally substituted" refers to a group which may or may not be further substituted with one or more groups selected from C1-6 alkyl, C2-6 alkenyl, C2-6 alkynyl, halo, halo C1-6alkyl, halo C2-6 alkenyl, halo C2-6 alkynyl, hydroxy, C1-6 alkoxy, C2-6 alkenyloxy, halo C1-6 alkoxy, haloalkenyloxy, nitro, nitro C1-6 alkyl, nitro C2-6 alkenyl, nitro C-6 alkynyl, nitroheterocyclyl, amino, C1-6 alkylamino, C1-6 dialkylamino, C2-6 alkenylamino, C2-6 alkynylamino, acyl, alkenylacyl, alkynylacyl, acylamino, diacylamino, acyloxy, C1-6 alkylsulphonyloxy, heterocyclyl, heterocyclyloxy, heterocyclylamino, haloheterocyclyl, C1-6 alkylsulphenyl, carboalkoxy, mercapto, C1-6 alkylthio, acylthio, phosphorus-containing groups and the like. Preferred optional substituents are methyl, ethyl, propyl, butyl, and phenyl.

The chain extender of formula (1) or formula (2) is preferably hydroxy-acetic acid 3-hydroxy-propyl ester, 6-hydroxy-hexanoic acid 2-hydroxyethyl ester, 6-hydroxyhexanoic acid 4-hydroxybutyl ester, ethylene glycol succinic acid diester diol, ethylene glycol fumaric acid diester diol, glycolic acid-ethylene glycol dimer, lactic acid-ethylene glycol dimer and mixtures thereof.

The chain extender of formula (1) of formula (2) may be prepared from one or more diols and one or more hydroxy acids and/or cyclic esters.

Non-limiting examples of the one or more diols include ethylene glycol, 1,3-propanediol, 1,2-propanediol, 1,4-butanediol, pentanediol, hexamethylenediol, heptanediol, octanediol, nonanediol, decanediol, dodecanediol, 2-ethyl-1,3-hexanediol (EHD), 2,2,4-trimethyl pentane-1,3-diol (TMPD), 1,4-cyclohexane dimethanol, diethylene glycol, dipropylene glycol, and combinations thereof. Non-limiting examples of hydroxy acids include l-lactic acid, d-lactic acid, d,l-lactic acid, mandelic acid, phenyl-lactic acid, hydroxybutyric acid, hydroxyvaleric acid or glycolic acid and combinations thereof. Non-limiting examples of cyclic esters include ε-caprolactone, glycolide, lactide, mandelide, and ρ-dioxanone and combinations thereof.

The polyurethane may further comprise one or more aliphatic polyol chain extenders which are hydrolytically non-degradable under in vivo conditions. For example, the polyurethane may further comprise one or more diol chain extenders which do not contain ester functionality in their backbones. Preferably, the non-degradable chain extender is an alkane diol having up to 30 carbon atoms, for example, ethylene glycol, 1,3-propanediol, 1,2-propanediol, 1,4-butanediol, pentanediol, hexamethylenediol, heptanediol, nonanediol, dodecanediol, 2-ethyl-1,3-hexanediol (EHD), 2,2,4-trimethyl pentane-1,3-diol (TMPD), 1,6-hexanediol, 1,4-cyclohexane dimethanol, diethylene glycol, dipropylene glycol, and mixtures thereof.
Liner Diisocyanates The aliphatic diisocyanate is preferably 4,4'-methylene dicyclohexyl diisocyanate (HMDI), 1,6-hexane diisocyanate (HDI), 1,4-butane diisocyanate (BDI), L-lysine diisocyanate (LDI), ethyl-L-lysine diisocyanate (ELDI), methyl-L-lysine diisocyanate (MLDI), 2,4,4-trimethylhexamethylenediisocyanate, other similar diisocyanates, and mixtures thereof.

The degradation products from aliphatic isocyanates (such as ethyl lysine diisocyanate (ELDI)) are generally considered to be more biocompatible than the degradation products from aromatic diisocyanates. Accordingly, isocyanates such as hexamethylene diisocyanate (HDI) and ELDI may be particularly suitable. Isophorone diisocyanate (IPDI) may also be used. Combinations of isocyanates may be used and may in some instances be preferable—for example, glass transition can be adjusted by combinations of HDI and IPDI. Trimethylhexamethylenediisocyanate, 1,4-butane diisocyanate, methyl-lysine diisocyanate (MLDI) and other isocyanates commonly used in polyurethane synthesis may also be suitable.

Liner Polyurethane Degradation

The polyurethane may contain hard and soft segments. The ratio of hard to soft segment influences the melting point of the polyurethane.

The hard segment content (% HS) of the polyurethane (that is, the combined content of the components derived from the chain extender of formula (1) or formula (2) and isocyanate, expressed by weight percentage) may range from 2 to 100 wt. %, or from 5 to 80 wt %, or from 10 to 70 wt %.

The soft segment content (% SS) of the polyurethane (that is, the percentage by weight of the components derived from the polyester polyol) may range from 5-98%, and in some embodiments, is at least 25% or at least 40%.

In some embodiments the polyurethane comprises hard and soft segments wherein the hard segment content (% HS) of the polyurethane is less than 60%, preferably between 30 and 60%.

The amount of chain extender of formula (1) or formula (2) in the polyurethane may be varied to vary the non-degradable length of continuous urethane in the hard segment. For example, the non-degradable length of the hard segment may have a molecular weight between 100 and 10,000 Daltons, or between 200 and 5,000 Daltons, or between 400 and 2,000 Daltons, or between 200 and 700 Daltons or between 320 and 700 Daltons.

The liner polyurethane may degrade, under the conditions of ASTM F1635, such that the number average molecular weight ($M_n$) of the polyurethane decreases by between 10% and 90% in a period of one year or less.

The liner polyurethane may be in vivo degradable. The polyurethane may be degradable at temperatures between 35 and 42° C.

Alternatively, the number average molecular weight ($M_n$) of the polyurethane may decrease by between 10% and 90% in a period of eleven months or less, or ten months or less, or nine months or less, or eight months or less, or seven months or less, or six months or less, or five months or less, or four months or less, or three months or less, or two months or less, or one month or less.

The rate of degradation, under the conditions of ASTM F1635, may be controlled through varying the nature and ratios of the components of the polyurethane. Accordingly, the polyurethane may be designed to degrade within a specific time period. This is advantageous in providing materials that are partially, fully, or substantially fully degradable in a specific time period, for example, when the functional aspects of the polyurethane are no longer required.

Melting Point

The melting point of the polyurethane of the liner may be between 60° C. and 190° C. The melting point may be between 60° C. and 180° C., or between 60° C. and 170° C., or between 60° C. and 160° C., or between 60° C. and 150° C., or between 60° C. and 140° C., or between 60° C. and 130° C., or between 60° C. and 120° C., or between 60° C. and 110° C., or between 60° C. and 100° C., or between 60° C. and 100° C., or between 60° C. and 90° C., or between 60° C. and 80° C., or between 60° C. and 70° C.

Where a clear melting transition occurs the melting point may be determined by differential scanning calorimetry. Other techniques know to those skilled in the art, such as dynamic mechanical thermal analysis, may also be utilised.

Adhesive

Various adhesives may be utilized to fix the liner to the foam. The adhesive layer may be a confluent layer or discontinuous layer. Suitable adhesives include, but are not limited to, solvent-based adhesives, latex adhesives, pressure-sensitive adhesives, hot-melt adhesives, and reactive adhesives, such as a biodegradable or non-biodegradable thermoset polyurethane reactive mixture. Suitable pressure-sensitive adhesives include, but are not limited to, pressure-sensitive adhesives made from acrylics, natural latexes, styrene-butadiene rubbers, and reclaimed rubbers. Suitable hot-melt adhesives include, but are not limited to, polyamides, polyolefins, and poly(ethylene-co-vinyl acetate).

In one embodiment, the liner may itself be an adhesive. In other embodiments, no adhesive may be utilised—the liner is melted directly onto the foam.

The biodegradable polyurethanes of the liner as herein disclosed may degrade by hydrolysis in vivo.

Manufacture of the Implant Pocket

In one embodiment the soft tissue implant pocket may be manufactured by folding a sheet of polyurethane foam, as disclosed herein, heat sealing the edges so as to fuse them together, but leaving an opening sized to introduce an implant of choice.

In another embodiment the soft tissue implant pocket may alternatively be manufactured by heat sealing together the edges of two sheets of polyurethane foam so as to fuse them together, but leaving an opening sized to introduce an implant of choice.

In another embodiment the soft tissue implant pocket may alternatively be manufactured by heat sealing two oversized sheets such that the heat seal follows between 50-80% of the circumference of a circle and then cutting out the remainder of the perimeter.

The sealing may be achieved through a combination of heat and pressure.

In another embodiment the soft tissue implant pocket may be manufactured by folding a sheet of polyurethane foam which has been laminated with a polyurethane liner, as disclosed herein, heat sealing the edges so as to fuse them together, but leaving an opening sized to introduce an implant of choice.

The folding may result in the liner being in the inside or the outside of the resulting pocket. Where the liner is located on the outside of the pocket, the pocket may be conveniently turned inside-out so that the liner is located on the inside of the pocket.

The liner may be laminated to the foam prior to forming the pocket so as there are substantially no gaps (for example, air bubbles) between the materials.

The foam layer and the liner layer may be of substantially equal dimensions of length and width.

The liner may be laminated to the foam through an interaction between the materials through the application of heat or pressure or a combination of heat and pressure. Alternatively, the liner may be covalently bonded to the foam. In an alternative and/or additional embodiment, the liner may be laminated to the foam layer with the aid of a suitable adhesive according to any of the aforementioned embodiments.

In another embodiment the implant pocket may be formed by fusing a layer of foam on each side of a liner so as to form a foam-liner-foam construct. The resulting construct may be folded and the sides fused together so as to leave an opening through which an implant may be introduced. The resulting pocket comprises inner and outer foam surfaces with a liner located therebetween. The liner may increase structural strength.

The liner may be formed by melt pressing.

The melt pressing may be performed at a temperature between 100 and 200° C.

The melt pressing may be performed at a pressure of up to 30 t.

The melt pressing may be performed between two smooth, or substantially smooth, sheets. The melt pressing may be performed between two PTFE sheets, for example glass fibre reinforced PTFE sheets.

Fusing of the liner to the foam may be performed in the absence of applied pressure.

The fusing may be performed by applying heat to the surface of the liner, for example by exposing the second major surface to a temperature between 100 and 200° C.

The fusing may be performed for a time between 5 seconds and minutes, preferably between 15 seconds and 90 seconds.

In another aspect of the present disclosure there is provided a method of preparing a soft tissue implant pocket comprising the steps of:
   (a) folding a polyurethane foam sheet, as herein disclosed, so as to substantially align the edges of the sheet; and
   (b) heat sealing the aligned edges leaving an opening sized for implant introduction.

In some embodiments the heat sealing is combined with cutting so as provide the final implant pocket.

In other embodiments cutting may be performed after heat sealing.

In another aspect of the present disclosure there is provided a method of preparing a soft tissue implant pocket comprising the steps of:
   (a) placing a first polyurethane foam sheet on a second polyurethane foam sheet such that the edges of the sheet are substantially aligned; and
   (b) heat sealing the aligned edges leaving an opening sized for implant introduction.

In another aspect of the present disclosure there is provided a method of preparing a soft tissue implant pocket comprising the steps of:
   (a) folding a foam/liner laminate, as herein disclosed, so as to substantially align the edges of the laminate; and
   (b) heat sealing the aligned edges leaving an opening sized for implant introduction.

In another aspect of the present disclosure there is provided a method of preparing a soft tissue implant pocket comprising the steps of:
   (a) folding a foam/liner/foam laminate, as herein disclosed, so as to substantially align the edges of the laminate; and
   (b) heat sealing the aligned edges leaving an opening sized for implant introduction.

In another aspect of the present disclosure there is provided a method of preparing a soft tissue implant pocket comprising the steps of:
   (a) placing a first polyurethane foam/liner laminate on a second polyurethane foam/liner laminate such that the edges of the laminate are substantially aligned; and
   (b) heat sealing the aligned edges leaving an opening sized for implant introduction.

In any one or more of the herein disclosed methods the foam layers may be bonded to each other or to liners through ultrasonic welding. This is a particularly useful method of bonding the layers where an oriented liner is utilized.

In an another aspect of the present disclosure there is provided use of a soft tissue implant pocket as disclosed herein for reducing or eliminating capsular contracture.

In another aspect of the present disclosure there is provided a method of reducing or eliminating capsular contraction comprising placing an implant in a soft tissue implant pocket as disclosed herein, sealing the pocket and implanting the pocket in a subject.

Further features and advantages of the present disclosure will be understood by reference to the following drawings and detailed description.

DESCRIPTION OF PREFERRED EMBODIMENTS

The following is a detailed description of the disclosure provided to aid those skilled in the art in practicing the present disclosure. Those of ordinary skill in the art may make modifications and variations in the embodiments described herein without departing from the spirit or scope of the present disclosure.

Although any methods and materials similar or equivalent to those described herein can also be used in the practice or testing of the present disclosure, the preferred methods and materials are now described.

It must also be noted that, as used in the specification and the appended claims, the singular forms 'a', 'an' and 'the' include plural referents unless otherwise specified. Thus, for example, reference to 'chain extender' may include more than one chain extenders, and the like.

Throughout this specification, use of the terms 'comprises' or 'comprising' or grammatical variations thereon shall be taken to specify the presence of stated features, integers, steps or components but does not preclude the presence or addition of one or more other features, integers, steps, components or groups thereof not specifically mentioned.

Unless defined otherwise, all technical and scientific terms used herein have the meaning commonly understood by a person skilled in the art to which this disclosure belongs.

Unless specifically stated or obvious from context, as used herein, the term "about" is understood as within a range of normal tolerance in the art, for example within two standard deviations of the mean. 'About' can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein in the specification and the claim can be modified by the term 'about'.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

The primary components and features used in the preparation of one or more embodiments of the soft tissue implant pocket as herein disclosed are discussed in detail in the following sections.

Examples of Preferred Embodiments

In one embodiment the present disclosure provides a soft tissue implant pocket wherein the polyurethane of the liner is derived from:
one or more chain extenders selected from hydroxy-acetic acid 3-hydroxy-propyl ester, 6-hydroxy-hexanoic acid 2-hydroxyethyl ester, 6-hydroxy-hexanoic acid 4-hydroxybutyl ester, ethylene glycol succinic acid diester diol, ethylene glycol fumaric acid diester diol, glycolic acid-ethylene glycol dimer and lactic acid-ethylene glycol dimer;
one or more aliphatic polyester polyols; and
one or more aliphatic diisocyanates;
wherein the polyurethane has a melting point between 60° C. and 190° C.; and
wherein the polyurethane of the foam or the liner degrades, under the conditions of ASTM F1635, such that the number average molecular weight ($M_n$) of the liner polyurethane and/or the mass of the foam independently decreases by between 10% and 90% in a period of one year or less.

In one embodiment the present disclosure provides a soft tissue implant pocket wherein the polyurethane of the liner is derived from:
one or more chain extenders selected from hydroxy-acetic acid 3-hydroxy-propyl ester, 6-hydroxy-hexanoic acid 2-hydroxyethyl ester, 6-hydroxy-hexanoic acid 4-hydroxybutyl ester, ethylene glycol succinic acid diester diol, ethylene glycol fumaric acid diester diol, glycolic acid-ethylene glycol dimer and lactic acid-ethylene glycol dimer;
one or more aliphatic polyester polyols; and
one or more aliphatic diisocyanates selected from 4,4'-methylene dicylcohexyl diisocyanate (HMDI), 1,6-hexane diisocyanate (HDI), 1,4-butane diisocyanate (BDI), L-lysine diisocyanate (LDI), 2,4,4-trimethylhexamethylenediisocyanate;
wherein the polyurethane has a melting point between 60° C. and 190° C.; and
wherein the polyurethane of the foam or the liner degrades, under the conditions of ASTM F1635, such that the number average molecular weight ($M_n$) of the liner polyurethane and/or the mass of the foam independently decreases by between 10% and 90% in a period of one year or less.

In one embodiment the present disclosure provides a soft tissue implant pocket wherein the polyurethane of the liner is derived from:
one or more chain extenders selected from hydroxy-acetic acid 3-hydroxy-propyl ester, 6-hydroxy-hexanoic acid 2-hydroxyethyl ester, 6-hydroxy-hexanoic acid 4-hydroxybutyl ester, ethylene glycol succinic acid diester diol, ethylene glycol fumaric acid diester diol, glycolic acid-ethylene glycol dimer and lactic acid-ethylene glycol dimer;
one or more aliphatic polyester polyols derived from one or more diol initiators and at least one hydroxy acid and/or cyclic ester; and
one or more aliphatic diisocyanates selected from 4,4'-methylene dicylcohexyl diisocyanate (HMDI), 1,6-hexane diisocyanate (HDI), 1,4-butane diisocyanate (BDI), L-lysine diisocyanate (LDI), 2,4,4-trimethylhexamethylenediisocyanate;
wherein the polyurethane has a melting point between 60° C. and 190° C.; and
wherein the polyurethane of the foam or the liner degrades, under the conditions of ASTM F1635, such that the number average molecular weight ($M_n$) of the liner polyurethane and/or the mass of the foam independently decreases by between 10% and 90% in a period of one year or less.

In one embodiment the present disclosure provides a soft tissue implant pocket wherein the polyurethane of the liner is derived from:
one or more chain extenders selected from hydroxy-acetic acid 3-hydroxy-propyl ester, 6-hydroxy-hexanoic acid 2-hydroxyethyl ester, 6-hydroxy-hexanoic acid 4-hydroxybutyl ester, ethylene glycol succinic acid diester diol, ethylene glycol fumaric acid diester diol, glycolic acid-ethylene glycol dimer and lactic acid-ethylene glycol dimer;
one or more aliphatic polyester polyols derived from one or more diol initiators and at least one hydroxy acid, diacid or cyclic ester, or combinations thereof, wherein the one or more diol initiators is selected from ethylene glycol, 1,3-propanediol, 1,2-propanediol, 1,4-butanediol, pentanediol, hexamethylenediol, heptanediol, nonanediol, dodecanediol, 2-ethyl-1,3-hexanediol (EHD), 2,2,4-trimethyl pentane-1,3-diol (TMPD), 1,6-hexanediol, 1,4-cyclohexane dimethanol, diethylene glycol, dipropylene glycol, and combinations thereof and wherein the at least one hydroxy acid is selected from l-lactic acid, d-lactic acid, d,l-lactic acid, mandelic acid, phenyl-lactic acid, valeric acid or glycolic acid; wherein the one or more diacids is selected from oxalic acid, malonic acid, succinic acid, glutaric acid, adipic acid, pimelic acid, suberic acid, azelaic acid, sebacic acid, undecanedioic acid, dodecanedioic acid, tridecanedioic acid, and hexadecanedioic acid and wherein the cyclic ester is selected from ε-caprolactone, glycolide, lactide, mandelide, and ρ-dioxanone; and
one or more aliphatic diisocyanates selected from 4,4'-methylene dicylcohexyl diisocyanate (HMDI), 1,6-hexane diisocyanate (HDI), 1,4-butane diisocyanate (BDI), L-lysine diisocyanate (LDI), 2,4,4-trimethylhexamethylenediisocyanate;
wherein the polyurethane has a melting point between 60° C. and 190° C.; and
wherein the polyurethane of the foam or the liner degrades under the conditions of ASTM F1635, such that the number average molecular weight ($M_n$) of the liner polyurethane and/or the mass of the foam independently decreases by between 10% and 90% in a period of one year or less.

Bioactive Substances

Bioactive substances may optionally be added to the polyurethanes of the foam, the liner or both.

The bioactive substance may be formulated with the polyurethane to form a composition. The formulation may be facilitated by, for example, melt processing, additive manufacturing or dissolution in an appropriate solvent.

Bioactive substances may be synthetic molecules, biomolecules, or multimolecular entities and include, but are not limited to, enzymes, organic catalysts, ribozymes, organometallics, proteins, glycoproteins, peptides, polyamino acids, antibodies, nucleic acids, steroidal molecules, antibiotics, silver, silver oxide, antivirals, antimycotics, anticancer agents, analgesic agents, antirejection agents, immunosuppressants, cytokines, carbohydrates, oleophobics, lipids, extracellular matrix and/or its individual components, demineralized bone matrix, hydroxyapatite, tricalcium phosphate, pharmaceuticals, chemotherapeutics, and therapeutics. Exogenous cells Cells and non-cellular biological entities, such as viruses, virus vectors and prions can also be bioactive substances. In one embodiment, the present disclosure provides a soft tissue implant pocket, wherein the implant pocket does not contain an added exogenous biological entity. The bioactive substances may be chemically bonded to the polyurethane.

The biological effect in humans or animals is for medical, therapeutic, cosmetic and veterinary purposes, and encompasses pharmaceuticals including drugs, cosmeceuticals, nutraceuticals, and nutritional agents. It will be appreciated that some of bioactive compounds can be classified in more than one of these classes.

A wide range of bioactive substances may be incorporated into the presently disclosed polyurethanes and may be consequently delivered with the soft tissue implant pocket as herein disclosed.

Examples include, but are not limited to, cardiovascular drugs, in particular antihypertensive agents (e.g. calcium channel blockers or calcium antagonists) and antiarrhythmic agents; congestive heart-failure pharmaceuticals; inotropic agents; vasodilators; ACE inhibitors; diuretics; carbonic anhydrase inhibitors; cardiac glycosides; phosphodiesterase inhibitors; α-blockers; n-blockers; sodium channel blockers; potassium channel blockers; β-adrenergic agonists; platelet inhibitors; angiotensin antagonists; anticoagulants; thrombolytic agents; treatments for bleeding; treatments for anaemia; thrombin inhibitors; antiparasitic agents; antibacterial agents; insulin; human growth hormone and peptides; vaccines; anti-inflammatory agents, in particular non-steroidal anti-inflammatory agents (NSAIDs), more particularly COX-2 inhibitors; steroidal anti-inflammatory agents; prophylactic anti-inflammatory agents; anti glaucoma agents; mast cell stabilisers; mydriatics; agents affecting the respiratory system; allergic rhinitis pharmaceuticals; a adrenergic agonists; corticosteroids; chronic obstructive pulmonary disease pharmaceuticals; xanthine-oxidase inhibitors; anti-arthritis agents; gout treatments; autacoids and autacoid antagonists; anti mycobacterial agents; antifungal agents; antiprotozoal agents; anthelmintic agents; antiviral agents especially for respiratory, herpes, cyto-megalovirus, human immunodeficiency virus and hepatitis infections; treatments for leukaemia and Kaposi's sarcoma; pain management agents in particular opioids, anaesthetics and analgesics; neuroleptics; sympathomimetic pharmaceuticals; adrenergic agonists; drugs affecting neurotransmitter uptake or release; anticholinergic pharmaceuticals; anti haemorrhoid treatments; agents to prevent or treat radiation or chemotherapeutic effects; lipogenesis drugs; fat reducing treatments; anti-obesity peptides; antiobesity agents such as lipase inhibitors; sympathomimetic agents; treatments for gastric ulcers and inflammation such as proton pump inhibitors; prostaglandins; VEGF inhibitors; antihyperlipidemic agents, in particular statins; drugs that affect the central nervous system (CNS) such as antipsychotic, antiepileptic and anti-seizure drugs (anticonvulsants), psychoactive drugs, stimulants, antianxiety and hypnotic drugs, antidepressant drugs; anti Parkinson's pharmaceuticals; hormones and fragments thereof such as sex hormones; growth hormone antagonists; gonadotropin releasing hormones and analogues thereof; steroid hormones and their antagonists; selective estrogen modulators; growth factors; anti diabetic pharmaceuticals such as insulin, insulin fragments, insulin analogues, glucagon like peptides and hypoglycaemic agents; H1, H2, H3 and H4 antihistamines; peptide, protein, polypeptide, nucleic acids and oligonucleotide pharmaceuticals; analogues, fragments and variants of natural proteins, polypeptides, oligonucleotides and nucleic acids and such like compounds; agents used to treat migraine headaches; asthma pharmaceuticals; cholinergic antagonists; glucocorticoids; androgens; antiandrogens; inhibitors of adrenocorticoid biosynthesis; osteoporosis treatments such as biphosphonates; antithyroid pharmaceuticals; cytokine agonists; cytokine antagonists; anticancer drugs; antialzheimer drugs; HMG-CoA reductase inhibitors; fibrates; cholesterol absorption inhibitors; HDL cholesterol elevating agents; triglyceride reducing agents; anti-ageing or anti-wrinkle agents; precursor molecules for the generation of hormones; proteins such as collagen and elastin; antibacterial agents; anti acne agents; antioxidants; hair treatments and skin whitening agents; sunscreens, sun protectants and filters; variants of human apolipoprotein; precursor molecules for generation of hormones; proteins and peptides thereof; amino acids; plant extracts such as grape seed extract; DHEA; isoflavones; nutritional agents including vitamins, phytosterols and iridoid gylcosides, sesquiterpene lactones, terpenes, phenolic glycosides, triterpenes, hydroquinone derivatives, phenylalkanones; antioxidants such as retinol and other retinoids including retinoic acid and co enzyme Q10; omega-3-fatty acids; glucosamine; nucleic acids, oligonucleotides, antisense pharmaceuticals; enzymes; cytokines; cytokine analogues; cytokine agonists; cytokine antagonists; immunoglobulins; antibodies; antibody pharmaceuticals; gene therapies; lipoproteins; erythropoietin; vaccines; small and large molecule therapeutic agents for the treatment, or prevention of human and animal diseases such as allergy/asthma, arthritis, cancer, diabetes, growth impairment, cardiovascular diseases, inflammation, immunological disorders, baldness, pain, ophthalmological diseases, epilepsy, gynaecological disorders, CNS diseases, viral infections, bacterial infections, parasitic infections, GI diseases, obesity, and haemological diseases.

It is to be understood that pharmaceutically, nutraceutically or cosmeceutically acceptable derivatives of bioactive substances are included within the scope of the present disclosure.

The term "pharmaceutically, nutraceutically or cosmeceutically acceptable derivatives" includes, but is not limited to, pharmaceutically, nutraceutically or cosmeceutically acceptable salts, esters, salts of such esters, ethers, or any other derivative including prodrugs and metabolites, which upon administration to a subject (e.g. patient, human or animal) in need is capable of providing, directly or indirectly, a bioactive substance as otherwise described herein.

As used herein, the term "pharmaceutically, nutraceutically or cosmeceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio.

Pharmaceutically, nutraceutically or cosmeceutically acceptable salts are well known in the art. For example, S. M. Berge, et al. describe pharmaceutically, nutraceutically or cosmeceutically acceptable salts in detail in J. Pharmaceutical Sciences, 66:1-1 9, 1977.

Examples of pharmaceutically, nutraceutically or cosmeceutically acceptable nontoxic acid addition salts are salts of an amino group formed with inorganic acids such as hydrochloric acid, hydrobromic acid, phosphoric acid, sulfuric acid and perchloric acid or with organic acids such as-acetic-acid, oxalic acid, maleic acid, tartaric acid citric acid, succinic acid, or malonic acid or by using other methods used in the art such as ion exchange.

Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hernisulfate, heptanoate, hexanoate, hydroiodide, 2 hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like.

Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate, and aryl sulfonate.

The term "pharmaceutically, nutraceutically or cosmeceutically acceptable ester" refers to esters which are hydrolysed in vivo and include those that break down readily in the human body to leave the parent compound or a salt thereof. Suitable ester groups include, for example, those derived from pharmaceutically, nutraceutically or cosmeceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of esters include formates, acetates, propionates, butyrates, acrylates and ethylsuccinates.

The term "pharmaceutically, nutraceutically or cosmeceutically acceptable prodrugs" as used herein includes those prodrugs of the biologically active substances which are, within the scope of sound medical judgment, suitable for use in contact with the tissues of a subject with undue toxicity, irritation, allergic response, and the like, commensurate with a reasonable benefit/risk ratio, and effective for their intended use, as well as the zwitterionic forms, where possible, of the biologically active substances.

The term "prodrug" refers to compounds that are rapidly transformed in vivo to yield a parent compound, for example by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987.

The present disclosure is further not limited solely to the administration of one biologically active substance: more than one biologically active substance or other therapeutic compounds may be incorporated into the foam layer and/or structural layer.

Degradation

The polyurethanes of either the foam or the liner (when present) or both of the soft tissue implant pocket of the present disclosure may be designed to degrade in vivo or under in vivo conditions at controlled rates. The polyurethanes may be degradable at temperatures between 35 and 42° C.

In some embodiments the number average molecular weight ($M_n$) of the liner polyurethane and the mass of the foam may independently decrease by between 20% and 90% in a period of eleven months or less, or ten months or less, or nine months or less, or eight months or less, or seven months or less, or six months or less, or five months or less, or four months or less, or three months or less, or two months or less, or one month or less.

In some embodiments the number average molecular weight ($M_n$) of the liner polyurethane and the mass of the foam may independently decrease by between 30% and 90% in a period of eleven months or less, or ten months or less, or nine months or less, or eight months or less, or seven months or less, or six months or less, or five months or less, or four months or less, or three months or less, or two months or less, or one month or less.

In some embodiments the number average molecular weight ($M_n$) of the liner polyurethane and the mass of the foam may independently decrease by between 40% and 90% in a period of eleven months or less, or ten months or less, or nine months or less, or eight months or less, or seven months or less, or six months or less, or five months or less, or four months or less, or three months or less, or two months or less, or one month or less.

In some embodiments the number average molecular weight ($M_n$) of the liner polyurethane and the mass of the foam may independently decrease by between 50% and 90% in a period of eleven months or less, or ten months or less, or nine months or less, or eight months or less, or seven months or less, or six months or less, or five months or less, or four months or less, or three months or less, or two months or less, or one month or less.

In some embodiments the number average molecular weight ($M_n$) of the liner polyurethane and the mass of the foam may independently decrease by between 60% and 90% in a period of eleven months or less, or ten months or less, or nine months or less, or eight months or less, or seven months or less, or six months or less, or five months or less, or four months or less, or three months or less, or two months or less, or one month or less.

In some embodiments the number average molecular weight ($M_n$) of the liner polyurethane and the mass of the foam may independently decrease by between 70% and 90% in a period of eleven months or less, or ten months or less, or nine months or less, or eight months or less, or seven months or less, or six months or less, or five months or less, or four months or less, or three months or less, or two months or less, or one month or less.

In some embodiments the number average molecular weight ($M_n$) of the liner polyurethane and the mass of the foam may independently decrease by between 80% and 90% in a period of eleven months or less, or ten months or less, or nine months or less, or eight months or less, or seven months or less, or six months or less, or five months or less, or four months or less, or three months or less, or two months or less, or one month or less.

In some embodiments the number average molecular weight ($M_n$) of the liner polyurethane and the mass of the foam may independently decrease by between 20% and 70% in a period of eleven months or less, or ten months or less, or nine months or less, or eight months or less, or seven months or less, or six months or less, or five months or less, or four months or less, or three months or less, or two months or less, or one month or less.

In some embodiments the number average molecular weight ($M_n$) of the liner polyurethane and the mass of the foam may independently decrease by between 30% and 70% in a period of eleven months or less, or ten months or less, or nine months or less, or eight months or less, or seven months or less, or six months or less, or five months or less, or four months or less, or three months or less, or two months or less, or one month or less.

In some embodiments the number average molecular weight ($M_n$) of the liner polyurethane and the mass of the foam may independently decrease by between 40% and 70% in a period of eleven months or less, or ten months or less, or nine months or less, or eight months or less, or seven months or less, or six months or less, or five months or less, or four months or less, or three months or less, or two months or less, or one month or less.

In some embodiments the number average molecular weight ($M_n$) of the liner polyurethane and the mass of the foam may independently decrease by between 50% and 70% in a period of eleven months or less, or ten months or less, or nine months or less, or eight months or less, or seven months or less, or six months or less, or five months or less, or four months or less, or three months or less, or two months or less, or one month or less.

In some embodiments the number average molecular weight ($M_n$) of the liner polyurethane and the mass of the foam may independently decrease by between 60% and 70% in a period of eleven months or less, or ten months or less, or nine months or less, or eight months or less, or seven months or less, or six months or less, or five months or less, or four months or less, or three months or less, or two months or less, or one month or less.

Figure 1:
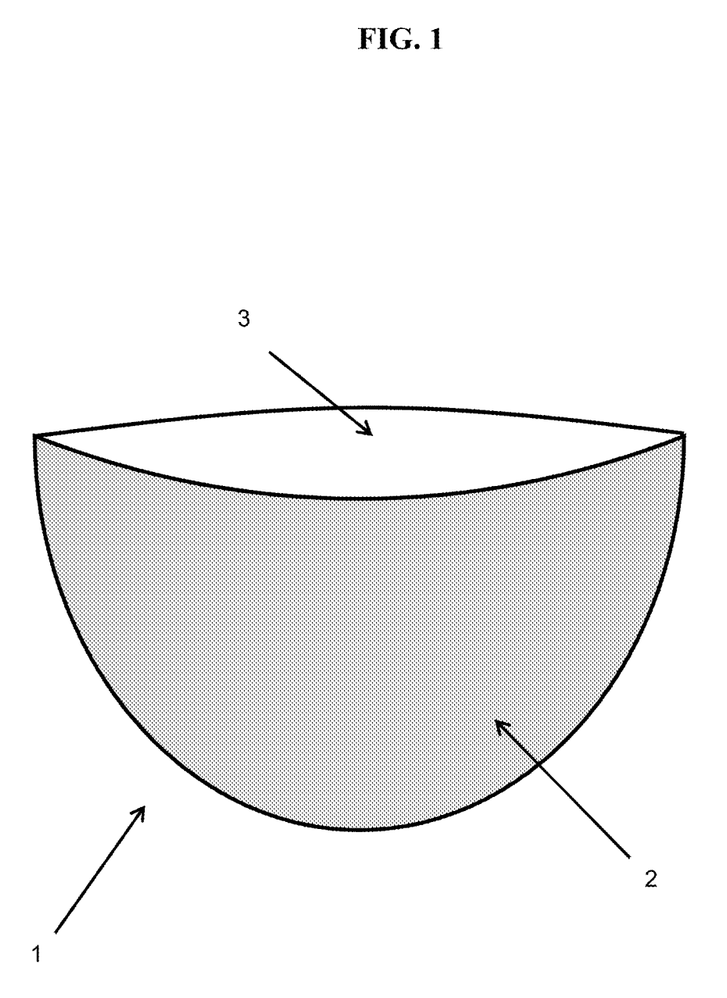
FIG. 1 is a schematic of a soft tissue implant pocket according to one embodiment of the present disclosure.

FIG. 1 illustrates a soft tissue implant pocket (1) according to an embodiment of the present disclosure comprising outer foam surface (2) and inner foam surface (3).

Figure 2:
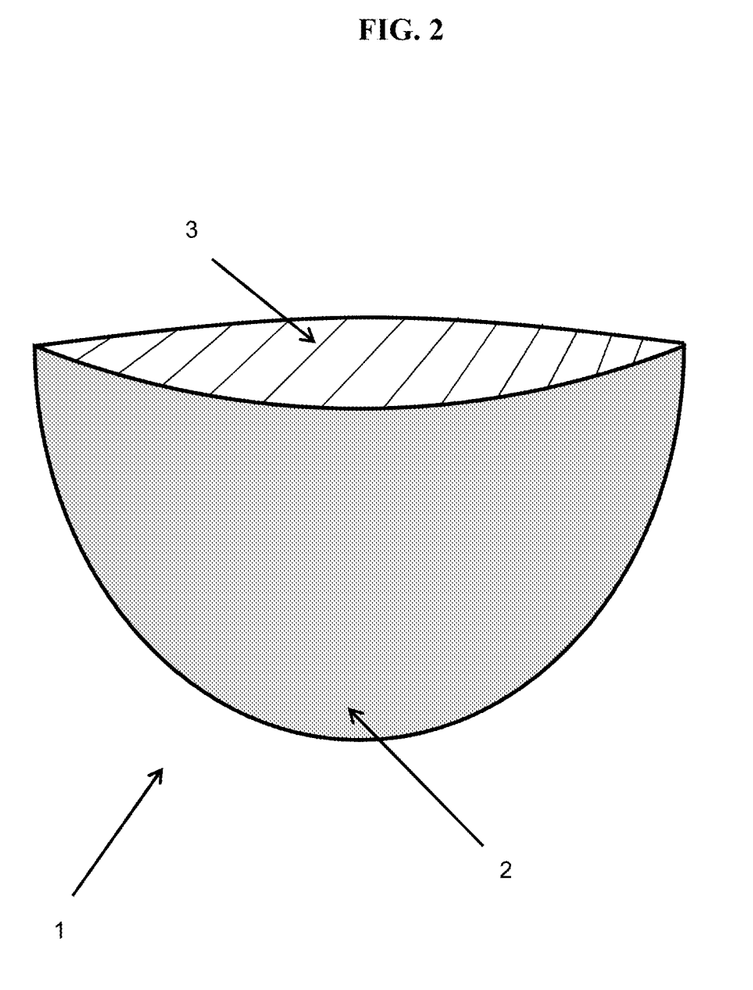
FIG. 2 is a schematic of a soft tissue implant pocket according to another embodiment of the present disclosure.

FIG. 2 illustrates a soft tissue implant pocket (1) according to an embodiment of the present disclosure comprising foam layer (2) and polyurethane liner (3).

The following Examples describe the preparation and use of the soft tissue implant pocket according to the present disclosure and are intended to illustrate the disclosure. The Examples are not to be construed as limiting in any way the scope of the present disclosure.

EXAMPLES

Foam Preparation

A biodegradable polyurethane foam was prepared according to the present disclosure. The foam was cut into sheets of 2 mm thickness using conventional foam slicing equipment.

Liner Preparation

Polyol Synthesis 3887 g of 1,4-butane diol (BDO), 3953 g of 90% lactic acid, and 10520 g of ε-caprolactone were added to a reactor fitted with stirring, condenser and a nitrogen atmosphere. The mixture was heated at 200° C. and heating was removed once the acid number was 1.9 mg KOH/g.

Chain Extender Synthesis 706.5 g ε-caprolactone and 2792.5 g BDO were added to a reactor fitted with heating and stirring. The mixture was heated at 200° C. until ε-caprolactone was no longer detectable by GC. GC testing of the product indicated 67.9% BDO, 26.7% dimer and 3.8% trimer.

Prepolymer Synthesis 6000.5 g of the above prepared polyol was charged to a reactor fitted with stirring and nitrogen and 3467.5 g 1,6-hexane diisocyanate (HDI) added. The mixture was heated to 60° C. and the reaction exotherm reached 90° C. The mixture was then cooled to 60° C. and 128.27 g of the above prepared chain extender and 0.2 g catalyst added. The exotherm reached 82° C. The NCO content of the prepolymer was found to be 7.607%.

Polymer Synthesis 9458.5 g of the above prepared prepolymer was weighed into a 20 litre container, and 771.5 g dry BDO added along with 0.7 g catalyst. The mixture was stirred and then poured into PTFE-lined trays and cured in an oven for a period of 2 hours at 120° C. The polymer was then granulated using a Zerma GSL 180/300 granulator.

Liner Fabrication

Polymer granules prepared as above were melt pressed between glass fibre-reinforced PTFE sheets at 175° C., 10 t pressure on a Carver press, to form a film 0.2 mm thick.

Manufacture of a Foam Pocket

In one example a 2 mm foam sheet prepared as above was folded so as to align the edges. The aligned edges were then heat treated so as to seal them together, however an opening, sized to receive an implant of choice, was left.

In another example, two 2 mm foam sheets prepared as above were aligned at the edges and the edges then heat treated so as to seal them together, however an opening, sized to receive an implant of choice, was left.

In one variant, the so-formed pocket was turned inside-out so that the heat sealed edge was now located inside the pocket.

Manufacture of a Foam Pocket Having a Polyurethane Liner

A 2 mm foam sheet prepared as above was applied to the top of the melt-pressed 0.2 mm liner sheet and heated on a melt-press platen without pressure at 175° C. for 45 seconds to bond the two layers together.

In one example the foam/liner laminate prepared as above was folded so as to align the edges and so that the liner surfaces were located on the inside. The aligned edges were then heat treated so as to seal them together, however an opening, sized to receive an implant of choice, was left.

In another example, two sheets of the foam/liner laminate prepared as above were aligned at the edges, so that the liner surfaces were located on the inside and the edges then heat treated so as to seal them together, however an opening, sized to receive an implant of choice, was left.

In another example, two sheets of the foam/liner laminate prepared as above were aligned at the edges, so that the liner surfaces were located on the outside and the edges then heat treated so as to seal them together, however an opening, sized to receive an implant of choice, was left.

In one variant, the so-formed pocket was turned inside-out so that the heat sealed edge was now located inside the pocket and the liner surface was located inside the pocket.

Manufacture of a Pocket from a Foam/Liner/Foam Laminate

A 1 mm thick foam sheet prepared as above was applied to the top of the melt-pressed liner and heated on a melt-press platen without pressure at 175° C. for 45 seconds to bond the two layers together. A second 1 mm thick foam sheet was applied to the exposed surface of the structural layer to form a laminate comprising a liner sandwiched between two foam layers.

In one example the foam/liner/foam laminate prepared as above was folded so as to align the edges. The aligned edges were then heat treated so as to seal them together, however an opening, sized to receive an implant of choice, was left.

In another example, two sheets of the foam/liner/foam laminate prepared as above were aligned at the edges, and the edges then heat treated so as to seal them together, however an opening, sized to receive an implant of choice, was left.

The contents of all references, and published patents and patent applications cited throughout the application are hereby incorporated by reference. Those skilled in the art will recognize that the disclosure may be practiced with variations on the disclosed structures, materials, compositions and methods, and such variations are regarded as within the ambit of the disclosure.

Those skilled in the art will recognize, or be able to ascertain using no more than routine experimentation, many equivalents to the specific embodiments and methods described herein. Such equivalents are intended to be encompassed by the scope of the following claims.

It is understood that the detailed examples and embodiments described herein are given by way of example for illustrative purposes only, and are in no way considered to be limiting to the disclosure. Various modifications or changes in light thereof will be suggested to persons skilled in the art and are included within the spirit and purview of this application and are considered within the scope of the appended claims. For example, the relative quantities of the ingredients may be varied to optimize the desired effects, additional ingredients may be added, and/or similar ingredients may be substituted for one or more of the ingredients described. Additional advantageous features and functionalities associated with the systems, methods, and processes of the present disclosure will be apparent from the appended claims. Moreover, those skilled in the art will recognize, or be able to ascertain using no more than routine experimentation, many equivalents to the specific embodiments of the disclosure described herein. Such equivalents are intended to be encompassed by the following claims.

The invention claimed is:

1. A human breast implant pocket comprising an inner surface, an outer surface and an opening shaped to receive a human breast implant, such that in use the implant pocket substantially covers the breast implant;
    wherein the pocket is an independent and distinct structure from the breast implant, and both the inner surface and the outer surface of the pocket comprise a biodegradable polyurethane thermoset foam, the biodegradable polyurethane thermoset foam comprising a pore structure configured for cellular infiltration with an average pore size in the range of from greater than 50 µm up to 600 µm;
    wherein the biodegradable polyurethane thermoset foam is derived from one or more biodegradable polyols having a molecular weight of less than or equal to about 10,000 Daltons and one or more isocyanates;
    the biodegradable polyurethane thermoset foam comprises less than 0.1 wt. % aromatic functionality; and
    the biodegradable polyurethane thermoset foam shrinks less than 20%, independently, in any single surface area after 10 days under in vivo condition; and
    wherein the implant pocket does not contain an added exogenous biological entity.

2. The human breast implant pocket according to claim 1, wherein the average pore size of the foam is between 100 µm and 300 µm.

3. The human breast implant pocket according to claim 1, wherein the polyurethane foam degrades, under the conditions of ASTM F1635, such that the mass of the foam decreases by between 10% and 90% in a period of one year or less.

4. The human breast implant pocket according to claim 1, wherein the polyurethane foam is derived from a mixture of one or more biodegradable polyols and one or more non-biodegradable polyols and one or more isocyanates.

5. The human breast implant pocket according to claim 4, wherein the one or more non-biodegradable polyols is a polyether polyol.

6. The human breast implant pocket according to claim 5, wherein the polyether polyol is selected from one or more of glycerol ethoxylate, glycerol propoxylate, glycerol ethoxylate-co-propoxylate, glycerol ethoxylate-block-propoxylate, pentaerythritol ethoxylate, pentaerythritol propoxylate, and trimethylolpropane propoxylate.

7. The human breast implant pocket according to claim 5, wherein the non-biodegradable polyols have a molecular weight of less than or equal to about 10,000 Daltons.

8. The human breast implant pocket according to claim 1, wherein the biodegradable polyols are polyester polyols.

9. The human breast implant pocket according to claim 1, wherein the biodegradable polyols are derived from one or more polyol initiators and one or more hydroxy acids, diacids or cyclic esters and combinations thereof.

10. The human breast implant pocket according to claim 1, wherein the pocket further comprises a polyurethane liner located on the inner surface of the pocket and sized to cover the inner surface of the pocket.

11. The human breast implant pocket according to claim 10, wherein the polyurethane liner is thermoplastic.

12. The human breast implant pocket according to claim 10, wherein the polyurethane liner is biodegradable.

13. The human breast implant pocket according to claim 10, wherein the liner has a thickness between about 20 µm and about 1000 µm.

14. The human breast implant pocket according to claim 1, wherein the pocket further comprises a polyurethane liner located between the inner foam surface and outer foam surface of the pocket.

15. A human breast implant comprising a soft tissue implant pocket according to claim 1 and a breast implant sealed within the pocket.

16. A method of reducing or eliminating capsular contraction comprising placing a breast implant inside the human breast implant pocket according to claim 1, sealing the pocket, and implanting the pocket containing the breast implant into a subject.

* * * * *